United States Patent [19]
Prescott

[11] Patent Number: 5,814,039
[45] Date of Patent: Sep. 29, 1998

[54] LASER CATHETER

[76] Inventor: Marvin A. Prescott, 833 Moraga Dr., Ste. 15, Los Angeles, Calif. 90049

[21] Appl. No.: 703,488

[22] Filed: Aug. 26, 1996

Related U.S. Application Data

[63] Continuation-in-part of Ser. No. 632,630, Apr. 15, 1996.

[51] Int. Cl.⁶ .............................. A61B 17/36; A61N 5/06
[52] U.S. Cl. .................... 606/7; 606/10; 606/27
[58] Field of Search ................. 606/2, 7, 9, 10, 606/11, 12, 14, 15, 16, 17

[56] References Cited

U.S. PATENT DOCUMENTS

| | | | |
|---|---|---|---|
| 4,676,246 | 6/1987 | Korenaga | 607/153 |
| 4,718,417 | 1/1988 | Kittrell et al. | 606/15 |
| 4,881,547 | 11/1989 | Danforth | 606/194 |
| 4,915,108 | 4/1990 | Sun | 607/96 |
| 4,930,504 | 6/1990 | Diamantopoulos et al. | 606/13 |
| 5,000,752 | 3/1991 | Hoskin et al. | 606/9 |
| 5,201,317 | 4/1993 | Kanazawa et al. | 606/15 X |
| 5,259,380 | 11/1993 | Mendes et al. | 607/115 |
| 5,261,904 | 11/1993 | Baker et al. | 606/17 |
| 5,272,716 | 12/1993 | Soltz et al. | 372/109 |
| 5,300,097 | 4/1994 | Lerner et al. | 607/93 |
| 5,334,171 | 8/1994 | Kaldany | 606/2 X |
| 5,344,419 | 9/1994 | Spears | 606/7 |
| 5,358,503 | 10/1994 | Bertwell et al. | 606/27 |
| 5,370,615 | 12/1994 | Johnson | 604/96 |
| 5,437,659 | 8/1995 | Leckrone | 606/7 |
| 5,470,352 | 11/1995 | Rappaport | 607/101 |
| 5,484,433 | 1/1996 | Taylor et al. | 606/17 |
| 5,616,140 | 4/1997 | Prescott | 606/10 |
| 5,620,438 | 4/1997 | Amplatz et al. | 606/10 |
| 5,624,433 | 4/1997 | Radisch, Jr. | 606/15 |

OTHER PUBLICATIONS

"GaInAsP/AlGaInP–Based Near–IR (780nm) Vertical–Cavity Surface–Emitting Lasers," by R.P. Schneider, Jr. et al., Electronics Letters, 30 Mar. 1995, vol. 31, No. 7, pp. 554–555.

*Primary Examiner*—Jennifer Bahr
*Assistant Examiner*—Sonya Harris-Ogugua
*Attorney, Agent, or Firm*—Graham & James LLP

[57] ABSTRACT

A laser catheter device includes a main housing containing a main lumen defined within its inner edge. The housing further includes one or more subsidiary lumens surrounding the main lumen. An electrically insulated strip lies along an outer edge of the housing. The strip contains several vertical cavity surface-emitting lasers powered by an external power source. The lead from the lasers to the power source extends through the subsidiary lumen. The device further includes an inflatable balloon surrounding the insulated strip and communicates with the main lumen. The balloon is inflated by an external source of inflation fluid.

22 Claims, 7 Drawing Sheets

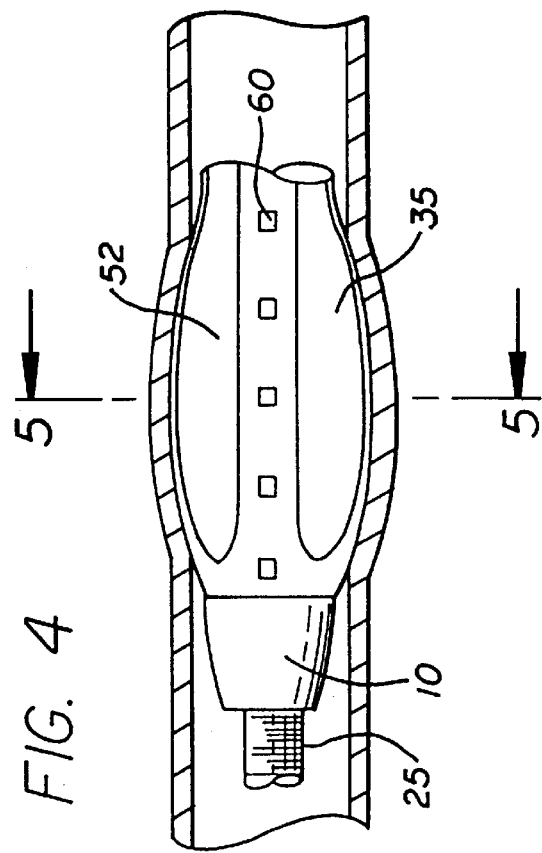
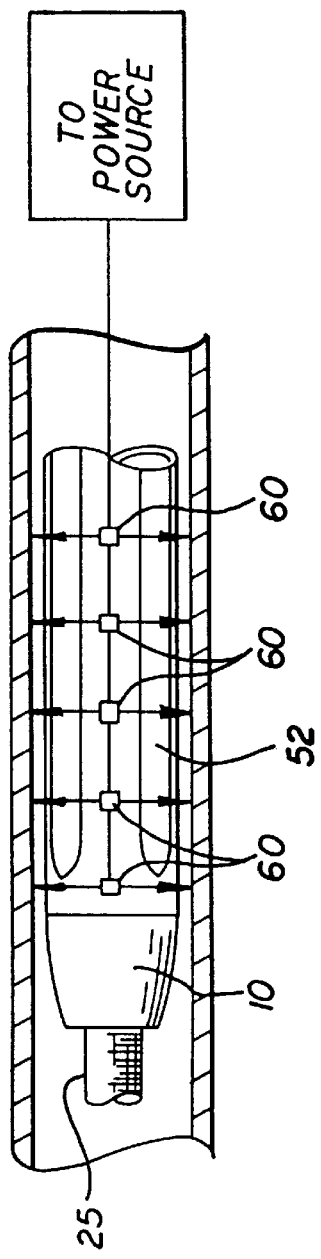
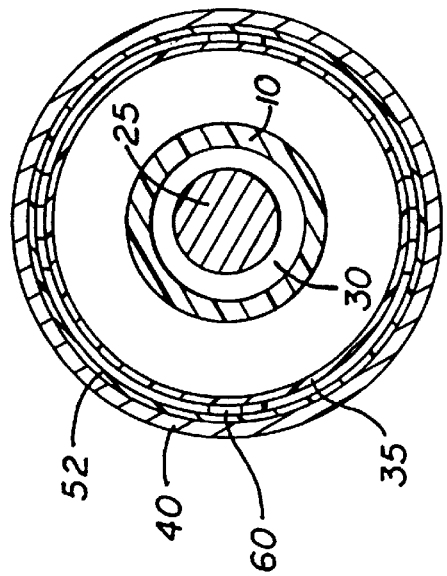

FIG. 7
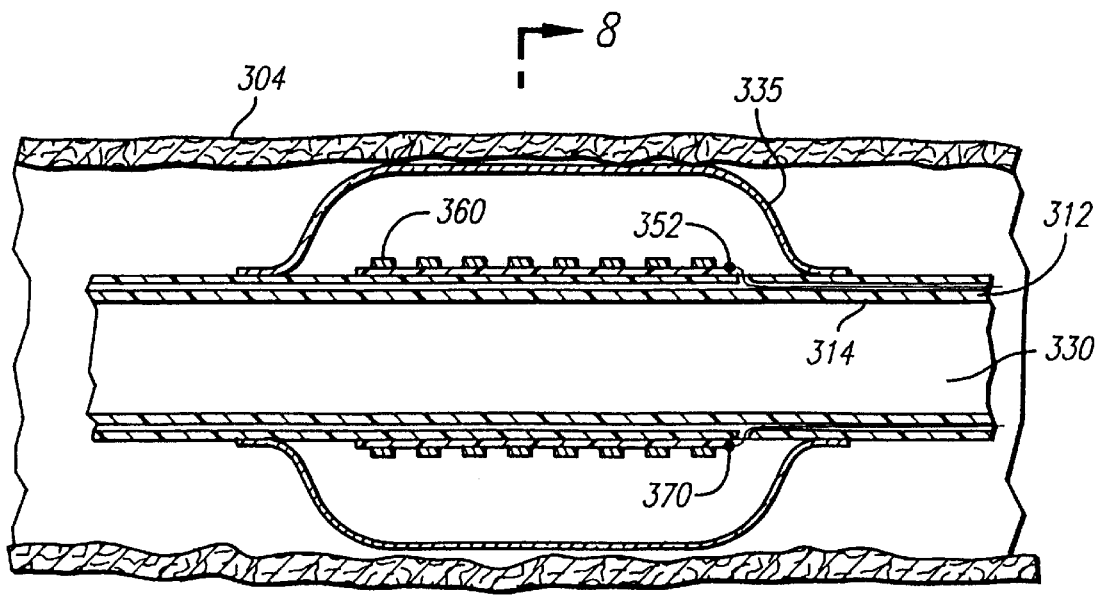
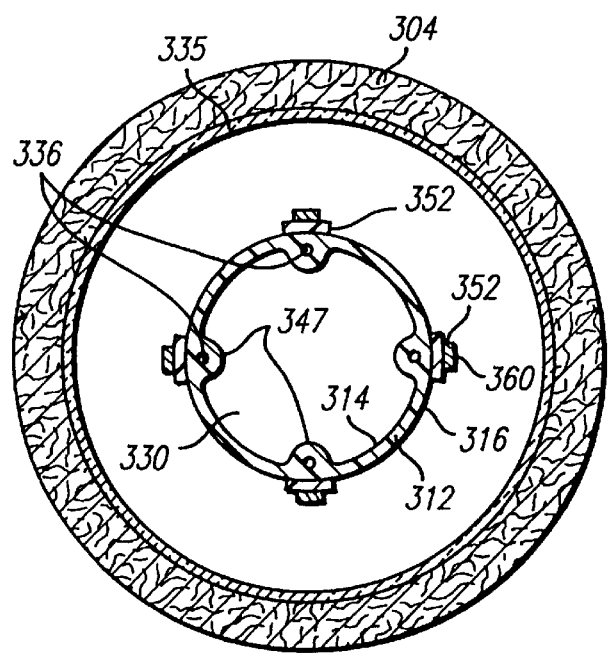
FIG. 8

LASER CATHETER

RELATED APPLICATIONS

This application is a continuation-in-part of U.S. patent application Ser. No. 08/632,630, filed Apr. 15, 1996, and entitled "Method and Apparatus for Laser Balloon Angioplasty Treatment of Medical Conditions."

BACKGROUND OF THE INVENTION

1. Field of the Invention

The present invention relates to a method and apparatus for balloon angioplasty treatment of medical conditions. More particularly, the present invention is directed to an apparatus for applying laser beam energy in a medical treatment regimen using a balloon angioplasty device in conjunction with electrically insulated flexible strips containing vertical cavity surface-emitting lasers capable of delivering a concentrated application of laser beam energy to a treatment area of an artery wall in a cost-effective and efficient manner.

2. Background

Balloon angioplasty is a known method for removing arteriosclerotic plaque from the lumen of affected arteries. At the outset of a routine percutaneous transluminal coronary angioplasty procedure, a preshaped angioplasty guiding catheter containing a balloon catheter equipped with a flexible intracoronary guidewire is engaged within the ostium of a coronary vessel containing the lesion to be dilated. Once suitably engaged (for example, within the left main or right coronary ostium), the guidewire is advanced within the lumen of the appropriate vessel and manipulated across the region of stenosis (narrowing). By rotating the guidewire, which contains a slight bend within its distal aspect, the operator can control the course of the wire, selecting the appropriate coronary lumen as the wire is advanced.

Once the wire is positioned across the region of stenosis, the angioplasty dilatation balloon catheter is advanced over the guidewire and positioned across the stenotic lesion. The angioplasty is accomplished by inflating the dilatation catheter to a high pressure, typically 6 to 10 atmospheres. Generally, 3 to 4 dilatations are required for each region of stenosis. Balloon inflation is maintained for 30 to 90 seconds during each dilatation, depending upon anatomic considerations and operator preference.

Following the final dilatation, the guidewire and balloon catheter are withdrawn leaving the guiding catheter in place. Selective coronary angiography then is performed to evaluate the cosmetic appearance of the vessel following the angioplasty and to determine the severity of the residual stenosis.

Balloon angioplasty, while an effective method for treating clogged arteries, has several known side effects. For instance, the enlarging of the artery and removal of the atherosclerotic plaque from the lumen can weaken the artery wall, potentially causing the wall to collapse. Furthermore, injury to the artery wall can cause scarring of the wall and subsequent incomplete healing of the endothelial wall. The scarred portions of the artery wall can then act as a site for rebuilding of the occluding plaque and reclogging of the affected artery. This reclogging process is called restenosis. The aforementioned side effects have been known to lead to a nearly 40% rate of restenosis following balloon angioplasty procedures and, thus, the need for additional expensive medical procedures.

Numerous methods for treating these side effects have been attempted. Molecular biology, drug therapy, the use of anti-platelet receptor anti-bodies, and the use of anti-sense oligonucleotides are the most common treatment procedures. Unfortunately, these methods can be prohibitively expensive. Moreover, studies show that such procedures do not significantly reduce the occurrence of restenosis.

Currently under investigation are various forms of radiation therapy. Under this proposed treatment, radioactive stents are used in healing the affected artery. This procedure has side effects as well, however. For example, the artery can potentially weaken following the treatment. More significantly, the prolonged exposure to radiation can be dangerous for attending hospital personnel and possibly lead to the development of cancer in the patient. In addition, stents have been known to cause abrupt thrombotic closure and hemorrhaging. The stents, themselves, can even become sites for the lodging and growth of resistant bacteria.

The application of laser beam energy in the treatment of medical conditions is known. Low power lasers, e.g., lasers having an energy output on the order of one milliwatt to 100 milliwatts and varying wavelengths, have been used since 1969 for medical and dental applications which include wound healing. Low level laser beam energy has been shown to enhance wound healing and reduce the development of scar tissue following surgical procedures, relieve stiff joints and promote the healing of injured joints, stimulate the body's ability to heal fractures and large contusions as well as enhancing the healing of difficult, slow-to-heal or non-healing decubitus or diabetic ulcers in patients.

Recent research has shown that the use of low power red laser light on rabbit aortas stimulates the wound-healing process following balloon angioplasty. The application of red laser light was shown to prevent the adverse balloon-induced changes that can occur, including neointimal smooth muscle cell proliferation. In addition, the application of laser energy to the affected area increased the rate and completeness of endothelial wall regeneration, thus resulting in a decreased rate of restenosis.

At present, however, there is no cost-effective device for the safe delivery of low power laser energy to arteries following balloon angioplasty. Accordingly, a need exists for an apparatus for applying low level laser energy to an affected artery following balloon angioplasty treatment. More particularly, a need exists for a cost-effective apparatus for applying the low level laser energy to the affected artery that will reduce weakening and collapse of the vessel, reduce neointimal smooth muscle cell proliferation, increase the rate of endothelial wall regeneration, reduce scarring of the vessel wall, and decrease or eliminate the rate of restenosis following balloon angioplasty treatment.

SUMMARY OF THE INVENTION

The present invention provides an apparatus for applying low level laser energy to an affected vessel following balloon angioplasty treatment. The present invention satisfies the need for a cost-effective method of laser treatment that reduces the current rate of restenosis following the treatment.

In a preferred embodiment, the apparatus of the present invention employs a catheter to be inserted into a vessel, such as an artery. An inflatable balloon surrounds a portion of the catheter near a distal end of the catheter. The catheter is connected to a tube which provides inflation fluid for inflating the balloon. A flexible pleated sleeve of clear silicone surrounds the balloon. Electrically insulated flexible film strips are embedded in the sleeve. The strips are aligned longitudinally along the outside of the balloon. Each strip contains a plurality of vertical cavity lasers connected in series. Power is provided to the lasers via an external power source so that each VCSEL emits approximately 1 to 10 milliwatts of power.

The present invention solves the problems of the prior art by providing a convenient, efficient, and effective mechanism for delivering laser beam energy for the purposes of treating an affected area of an artery wall. During the balloon angioplasty treatment, the device is inserted into the vessel and the balloon is expanded. The flexible sleeve surrounding the balloon expands to accommodate the balloon. The longitudinally-aligned electrically insulated flexible strips remain disposed along the top, bottom, and sides of the balloon when inflated. When power is applied to the lasers, low level laser energy is transmitted to the vessel continuously for five to ten minute periods. Thus, the present invention does not require a sophisticated and expensive mechanism for delivering the laser energy directly to the affected area.

By providing a device for applying low level laser energy to the treated artery, which energy is known to decrease neointimal smooth muscle cell proliferation and stimulate the wound-healing process, the rate of restenosis can be decreased. Further, by stimulating the wound healing process, such treatment can also help to reduce the additional attendant side effects associated with the balloon angioplasty treatment.

A more complete understanding of the laser catheter will be afforded to those skilled in the art, as well as a realization of additional advantages and objects thereof, by a consideration of the following detailed description of the preferred embodiment. Reference will be made to the appended sheets of drawings which will first be described briefly.

BRIEF DESCRIPTION OF THE DRAWINGS

FIG. 3 is a side view of the catheter of the present invention with the balloon in the unexpanded state.

FIG. 4 is a side view of the catheter of the present invention with the balloon in an expanded state.

FIG. 5 is a forward view of the catheter of the present invention with the balloon in an expanded state.

FIG. 7 a side view of a third embodiment of the catheter of the present invention.

FIG. 8 is a forward view of the third embodiment of the catheter of the present invention.

DETAILED DESCRIPTION OF THE PREFERRED EMBODIMENT

Figure 1:
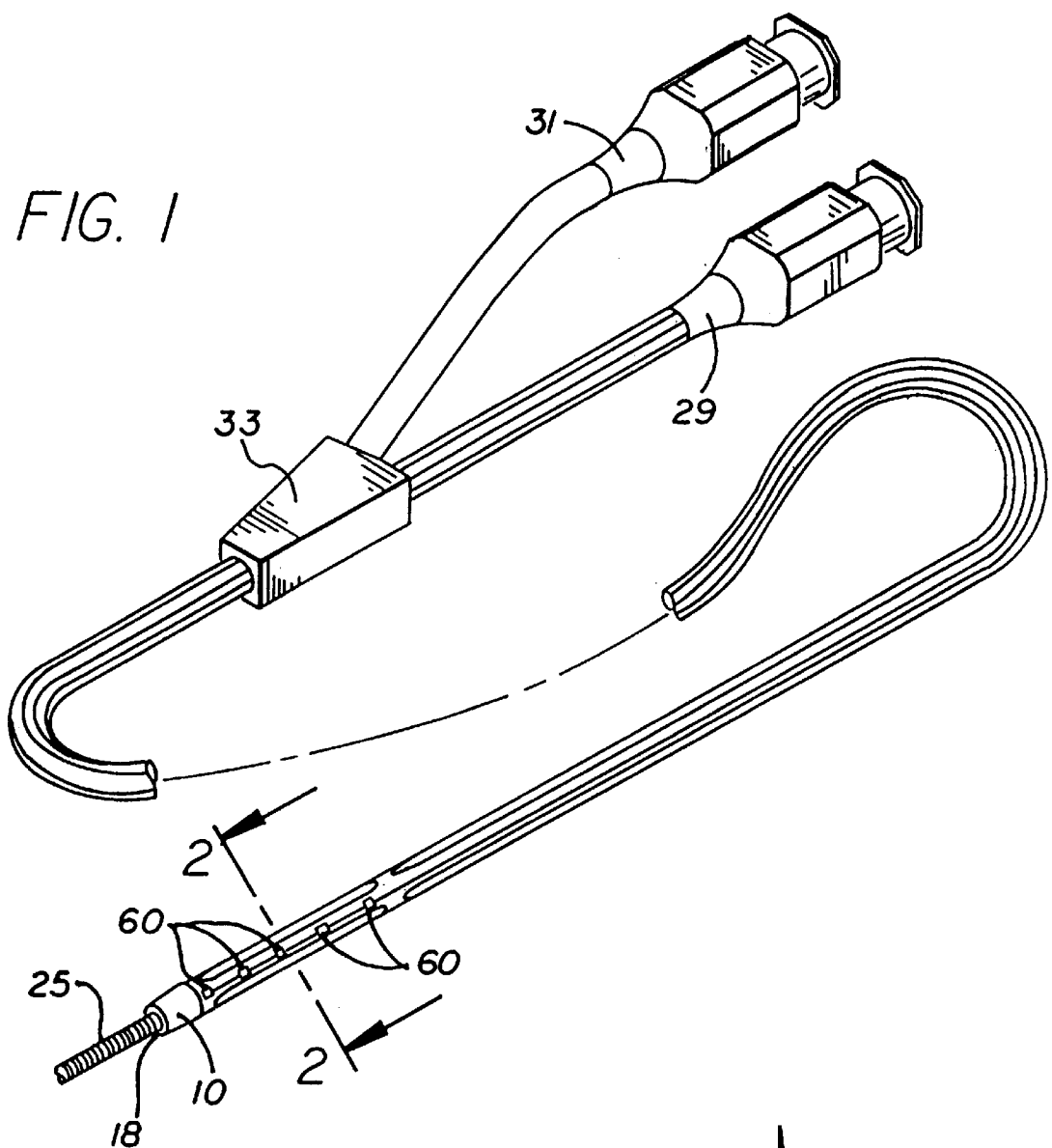
FIG. 1 perspective view of a preferred embodiment of the catheter of the present invention.

FIGS. 1–4 illustrate a first preferred embodiment of the present invention. It should be understood that the following discussion of the presently preferred embodiments is not to be considered in a limiting sense. Rather, it is to be understood that numerous modifications, additions, and/or substitutions can be made to the preferred embodiments without departing from the spirit and scope of the present invention.

A laser balloon angioplasty device in accordance with the first preferred embodiment of the present invention includes a catheter 12 having a housing 10 extending from a proximal end (not shown) to a distal end 18. The housing 10 is generally cylindrical and is comprised of flexible plastic or a similarly resiliently flexible material. The distal end 18 of the housing 10 is made in accordance with a dual lumen design. The space between the inner wall 15 of the housing and the outer edge 17 of the guidewire 25 defines a dual guidewire/inflation lumen 30 having a guidewire 25 therein. The dual lumen 30 is generally annular in cross section. The guidewire 25 is comprised of stainless steel or platinum or an equivalent thereof.

As shown in FIG. 1, the catheter 12 includes a tube 29 that provides inflation fluid to the balloon 35. Inflation fluid is evacuated through tube 31. The inflation tube 29 and evacuation tube 31 combine at junction box 33 to communicate with the dual lumen 30. The dual lumen 30 communicates with the interior of a balloon 35 located near the distal end 18 of the catheter. The balloon 35 typically is formed from an inelastic material to permit uniform inflation to a predetermined volume. The balloon 35, when inflated with inflation fluid fed from an inflation tube 37 that communicates with the dual lumen 30, expands to apply therapeutic outward pressure against the interior walls of an occluded blood vessel in which the balloon 35 is positioned. Inflation fluid is removed utilizing a removal tube 39 that communicates with the dual lumen 30.

The wall thickness of the housing 10 is approximately 0.002–0.003 inches. The total outside diameter of the balloon catheter, other than in the region of the balloon 35 itself, is about 0.040 inches. The balloon catheter is made of synthetic material such as nylon.

Figure 2:
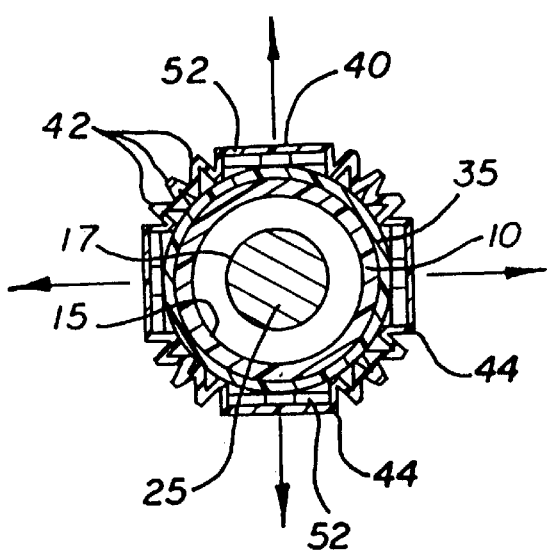
FIG. 2 is a front view of the catheter of the present invention.

As shown in detail in FIG. 2, a flexible sleeve 40 surrounds the balloon 35 near the distal end 18 of the catheter. The sleeve 40 has a thickness of approximately 0.25–0.50 mm and is preferably formed of optically transparent soft silicone or a similar biocompatible polymer material. The sleeve 35 is molded to accommodate balloon catheters of different sizes. When the balloon 35 is not inflated, the sleeve 40 fits tightly over the balloon 35. The sleeve 40 contains flat portions 44 along the top, bottom, and sides of the balloon to accommodate insulated strips 52 embedded therein. To accommodate the expansion of the balloon 35, the sleeve 40 contains pleats 42. When the balloon 35 is in its expanded state (shown in FIG. 4), the pleats 42 expand to permit the flat portions 44 of the sleeve 40 to maintain the same orientation with respect to the balloon 35 as in the uninflated state. The transparent soft silicone material permits the transfer of laser energy therethrough, as described below.

Four electrically insulated flexible film strips 52 are embedded into the flat rectangular portions of the sleeve 40 adjacent to the balloon 40. Each electrically insulated film strip has a thickness of approximately 0.003 inches. The strips 52 are aligned longitudinally along the outer circumference of the balloon 35. Accordingly, the length of each strip is approximately the same length as the balloon. This length will vary depending upon the length of the balloon.

Each strip 52 is preferably formed of a polyester insulated material, such as polyetherimide or polyimide film. Suitable polyetherimide material is sold, for example, by General Electric Co. under the trademark Ultem. Suitable polyimide film is sold, for example, by DuPont Co. under the trademark Kapton. In the uninflated state, the insulated film strips are aligned along the top, bottom, and sides of the balloon in the flat portions 44 of the sleeve 40. When the balloon 35 is filled with inflation fluid via the distal inflation lumen 30, the flexible nature of the sleeve allows the insulated film strips to maintain this orientation. Each strip 52 is electrically insulated and includes electrical interconnections etched along the surface. The various interconnections permit the surface-mounting of various electrical devices, including vertical surface-emitting laser chips, on the strip 52.

Up to 8 vertical surface-emitting laser ("VCSELs") chips 60 are surface-mounted onto each strip 52. Each chip 60 is approximately 2 millimeters long and the chips 60 are spaced approximately 3 millimeters apart along the surface of each strip 52. Each 2 millimeter long VCSEL chip 60 contains up to 8 VCSEL laser wells. Each laser has a nominal operating power output of 4.2 milliwatts and a wavelength on the order of 600–800 nanometers, with the preferred wavelength being approximately 780 nanometers. The preferred power output of each VCSEL ranges from 1 to 8.2 milliwatts. However, the inventor has found that 4 milliwatts represents a preferred operating level that affords sufficient power for laser treatments having a duration of 5–10 minutes.

Vertical cavity surface-emitting lasers are known and comprise lasers which emit a collimated beam normal to the surface of the semiconductor substrate. The semiconductor typically comprises aluminum arsenide (AlAs) or gallium arsenide (GaAs), or a combination thereof. Each VCSEL has a self-contained, high-reflectivity mirror structure forming a cavity which produces a collimated beam. While particular applications of the present invention may require a more focused or less focused beam, the preferred embodiment uses the beam directly from the VCSELs. The beam may be further focused or defocused utilizing a microlens incorporated into the VCSEL. A typical VCSEL may be on the order of 300 micrometers long.

The VCSEL chips 60 are disposed on each insulated film strip 52 as shown in FIG. 3. Each strip 52 contains 4–8 VCSEL chips spaced 3 millimeters apart and connected through the sleeve 40 to an external power source 72 via a lead 62. The chips of VCSELs are interconnected with flexible electrical connectors etched on the strip 52. Preferably, the VCSEL chips 60 in each strip 52 would be electrically connected in series. The strips 52 would then be connected together in parallel.

Figure 6:
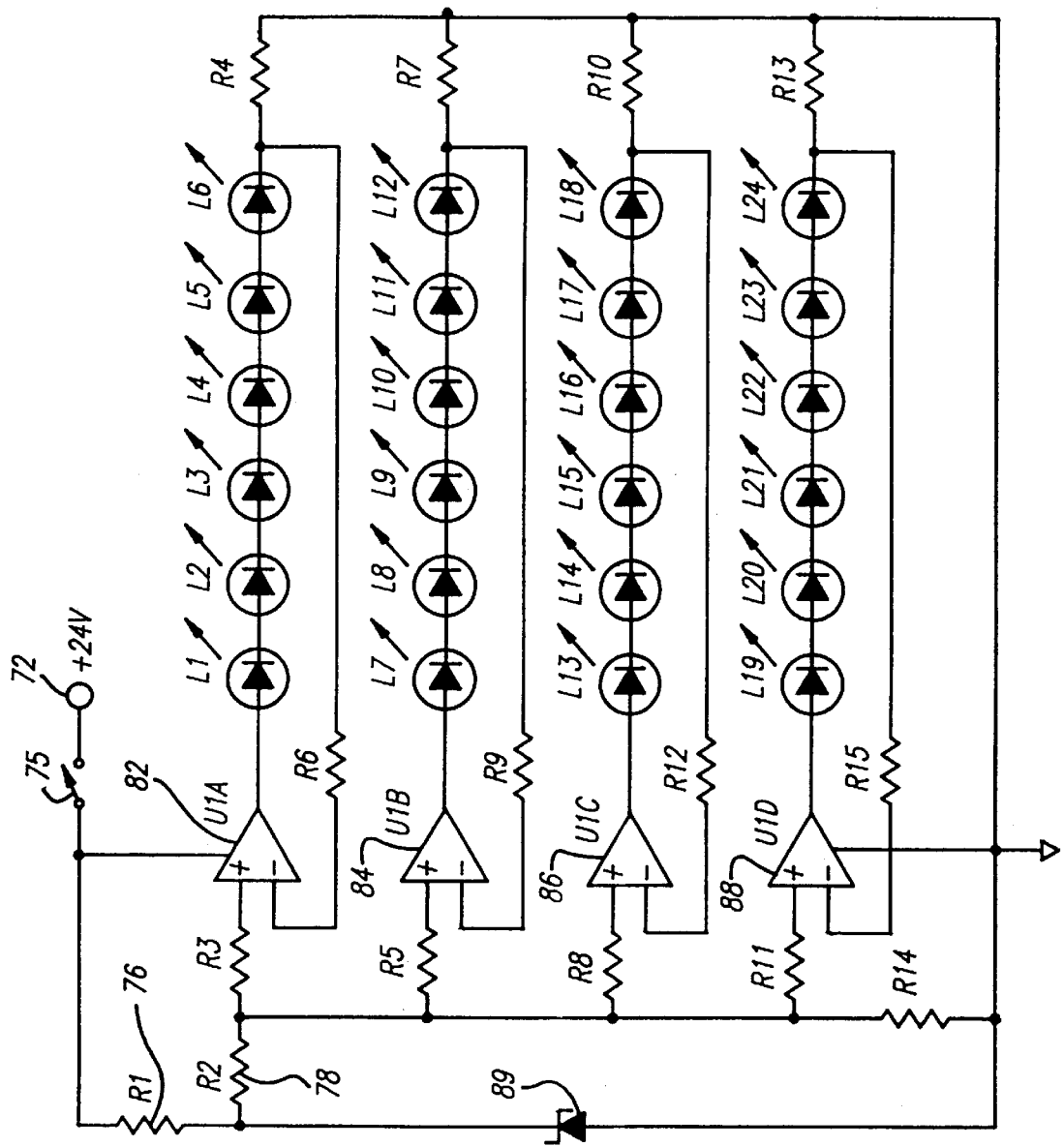
FIG. 6 is a circuit diagram of a laser therapy control circuit utilized with the catheter of the present invention.

A preferred embodiment of a laser angioplasty therapy control circuit 70 is shown in FIG. 6. As shown, an external power source 72 supplies a potential of 3 volts to the circuit via a switch 75. The power source 72 is connected through switch 75 to resistors 76, 78. The voltage is regulated through resistors 76, 78 which regulate the voltage to noninverting operational amplifiers 82, 84, 86, 88. Op-amps 82, 84, 86, 88 regulate voltage to VCSELs 60. The voltage is further regulated by zener diode 89. Other types of power control circuits that can be utilized are shown, for example, in U.S. application Ser. Nos. 08/136,382 and 08/215,263, both by M. Prescott, filed Oct. 12, 1993 and Mar. 21, 1994, respectively, the disclosure of which are hereby incorporated by reference.

The laser balloon angioplasty treatment is performed by inserting the balloon angioplasty device into the affected artery proximate the region of stenosis. In the uninflated state, the strips 52 are aligned along the top, bottom, and sides of the balloon 35. Inflation fluid is provided through the inflation lumen 30 to the balloon 35. As the balloon 35 fills with fluid, it gradually expands to open the artery near the region of stenosis. While the balloon 35 is expanded, as shown in FIG. 5, the switch 75 is activated to provide power to the laser therapy control circuit 70. As shown in FIG. 4, the VCSEL strips 52 remain aligned along the top, bottom, and sides of the balloon 35 in the flat portions 44 of the sleeve 40. The VCSELs contained in each VCSEL chip 60 emit a low power laser beam through the optically clear silicone sleeve 40. The sleeve 40 may be composed of any biocompatible polymer. The low power laser energy is preferably to be applied for a period of five to ten minutes. The laser energy stimulates the affected area to improve healing and reduce restenosis and neointimal smooth muscle cell proliferation.

A second embodiment of the present invention is described, but not shown. In this embodiment, a non-expandable catheter having distal and proximal ends is utilized. A flexible sleeve surrounds the catheter near the distal end of the catheter. Four electrically insulated flexible strips surround the catheter and are embedded in the flexible sleeve. The strip contains VCSEL chips embedded therein throughout its area. The configuration of the VCSEL chips are similar to the VCSEL chips described with respect to the first embodiment. Each VCSEL has a nominal power output of 2.6 milliwatts and a wavelength on the order of 600–800 nanometers, with the preferred wavelength being approximately 780 nanometers. Preferably, the VCSEL chips in the strip would be electrically connected in series.

FIGS. 7 and 8 show a third embodiment of the catheter of the present invention as contained within an aterial wall 304. The third embodiment uses a multi-lumen design to facilitate the delivery of electrical power to the VCSELs. More particularly, this embodiment includes a cylindrical catheter housing 312 having an inner edge 314 and an outer edge 316. The opening within the inner edge 314 defines an inflation and guidewire lumen 330. A plurality of extensions 347 extend from the circumference of the housing 312 to the inflation lumen 330. Each extension 347 includes an additional lumen 336 that extends along the length of the catheter housing 312.

A plurality of insulated polyester strips 352 are disposed longitudinally along the outer edge 316 of the catheter housing 312. Suitable polyester material includes Kapton or Ultem, although other insulated material may be used. Each strip 352 has a preferred height from the outer edge 316 of approximately 0.002 inches. The width of each strip is approximately one millimeter. Each strip 352 is bonded or welded to the shaft using known methods. A plurality of VCSELs chips 360 are surface-mounted onto each strip 352 as described above with respect to the first embodiment. Each strip 352 may further include a plurality of focusing lenses (not shown) to focus the laser emitted by each VCSEL chip 360. The VCSELs are powered by an external power source (not shown) via a lead 370 extending from an end of each insulated strip 352. Each lead 370 exits the catheter 312 to the power source through an adjacent lumen 336 extending beneath the conductive strip 352. The preferred power source is the control circuit shown in FIG. 6.

An inflatable balloon 335 surrounds the polyester strips 352. The inflatable balloon is in fluid communication with the inflation lumen 330. The catheter is operated as discussed above with laser energy from the VCSELs 360 penetrating the balloon 335 and treating the affected area of the arterial wall 304. The catheter is operated as discussed above with respect to the first embodiment.

Figure 9:
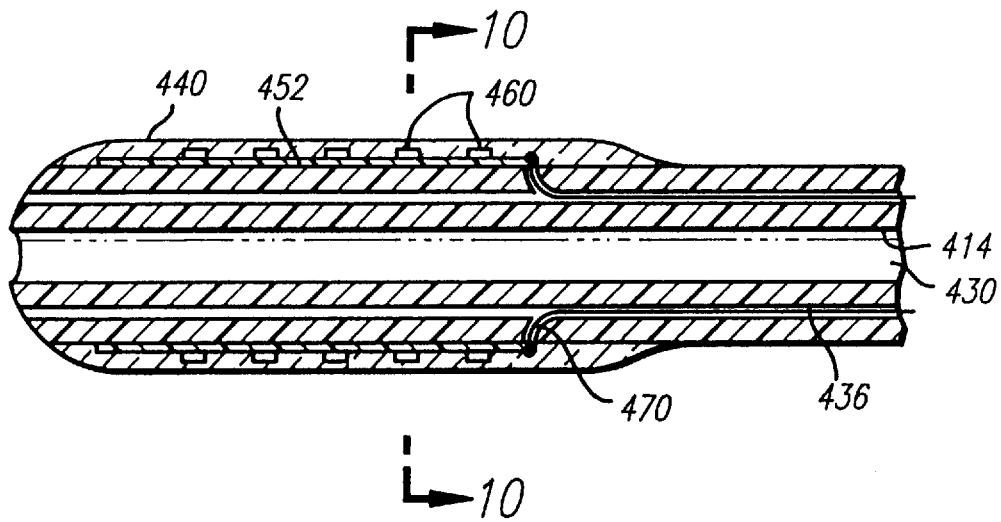
FIG. 9 is a side view of a fourth embodiment of the cathether of the present invention.
Figure 10:
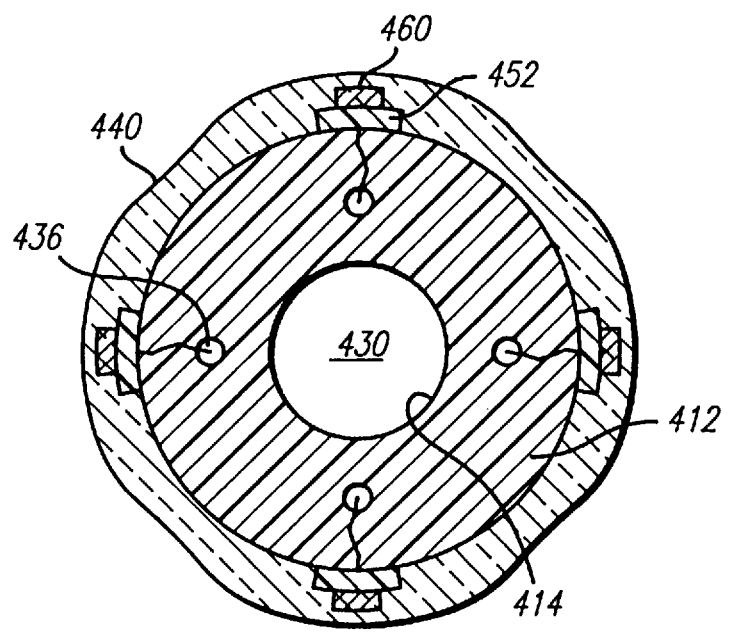
FIG. 10 is a forward view of the fourth embodiment of the catheter of the present invention.

FIGS. 9 and 10 show a fourth embodiment of the catheter of the present invention. The fourth embodiment uses a multi-lumen design, but does not include the inflatable balloon of the previous embodiments. The catheter housing 412 is cylindrical and includes a main guidewire lumen 430 defined within an inner edge 414 of the housing 412 and a plurality of internal lumens 436 arranged within the interior of the housing 412 and surrounding the main lumen 430. A guidewire (not shown) may be disposed within the main guidewire lumen 430.

A plurality of insulated polyester strips 452 are disposed along an outer edge 416 of the catheter housing 412. Each strip 452 is bonded or welded to the housing 412 using known methods. A plurality of VCSELs chips 460 are surface-mounted onto each strip 452. Each strip 452 may further include a plurality of focusing lenses to focus the laser emitted by each VCSEL chip 460. The VCSELs are powered by an external power source (not shown) via a lead 470 extending from an end of each insulated strip 452. Each lead 470 exits the catheter 412 to the power source through an adjacent lumen 436. An optically clear soft silicone sleeve 440 (or other optically clear biocompatible material) surrounds the catheter 412 and insulated strips 452. The catheter is operated as discussed above with laser energy from the VCSELs 460 penetrating the silicone sleve 440.

Figure 11:
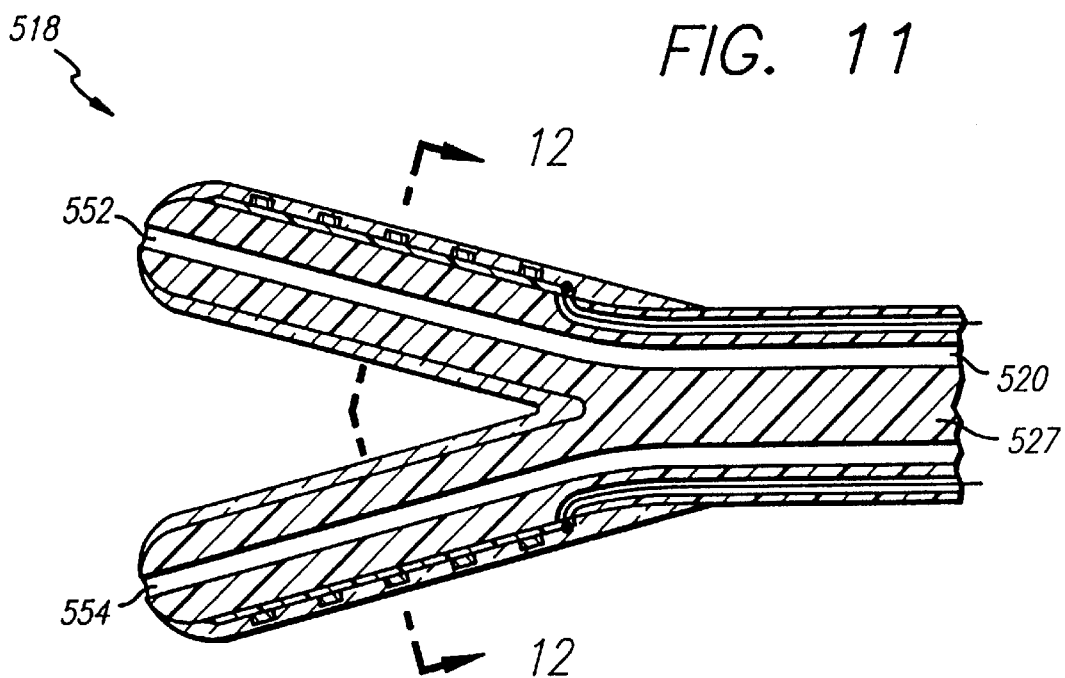
FIG. 11 is a side view of a fifth embodiment of the catheter of the present invention.
Figure 12:
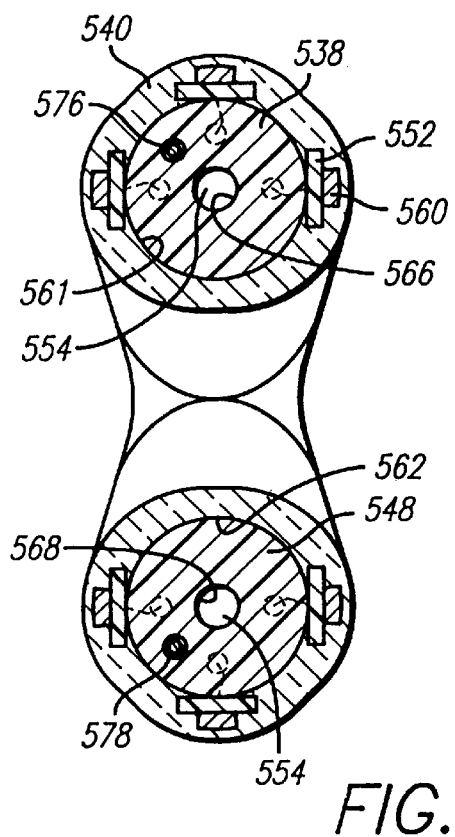
FIG. 12 is a forward view of the fifth embodiment of the catheter of the present invention.

FIGS. 11 and 12 show a fifth embodiment of the catheter of the present invention. In particular, a split catheter is used. The catheter housing 512 extends from a distal end (not shown) to a proximate end 518. At the distal end, the catheter includes a single lumen 520 surrounding an inner housing member 527. At a point near the proximate end 518, the inner housing member 527 splits into a "Y" shape to produce two separate housings 538, 548. Each housing 538, 548 is defined by an outer edge 561, 562 and an inner edge 566, 568. Each housing 538, 548 includes a lumen 552, 554 in communication with the main lumen 520. A plurality of additional lumens 566 are disposed circumferentially around each housing and extending longitudinally through each housing. Further, each housing 538, 540 includes a guidewire lumen 576, 578. A guidewire 588, 590 extends from the distal end of the catheter to the proximate end 518 through a respective guidewire lumen.

A plurality of insulated polyester strips 552 are disposed along the outer edge 560, 562 of each catheter housing 538, 540. Each strip 552 is bonded or welded to the housing using known methods. A plurality of VCSELs chips 560 are surface-mounted onto each strip 452. Each strip 552 may further include a plurality of focusing lenses to focus the laser emitted by each VCSEL chip 560. The VCSELs are powered by an external power source (not shown) via a lead 570 extending from an end of each insulated strip 552. Each lead 570 exits the catheter 512 to the power source through an adjacent lumen 536.

Figure 13:
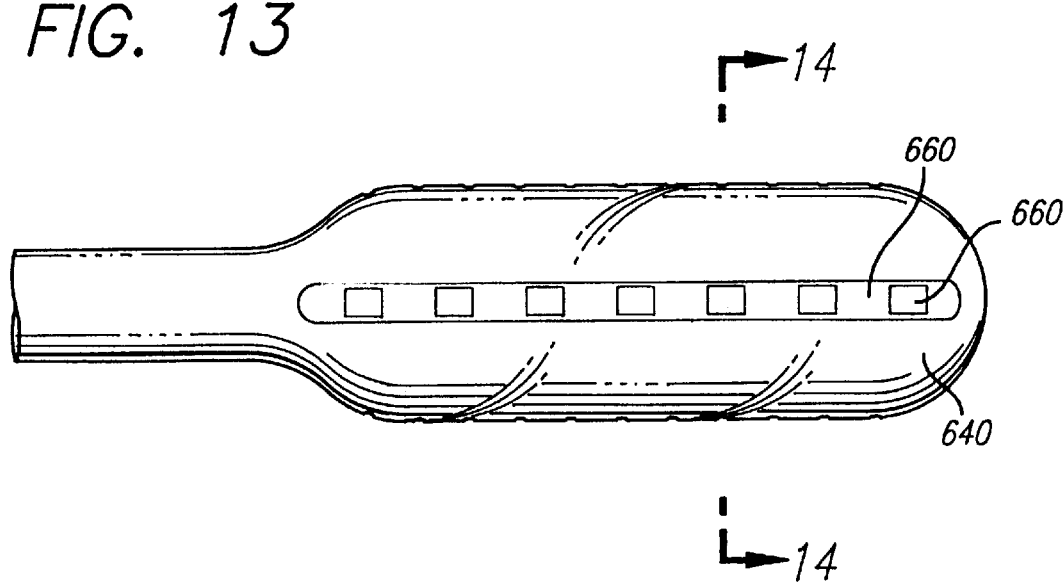
FIG. 13 is a side view of a sixth embodiment of the catheter of the present invention.
Figure 14:
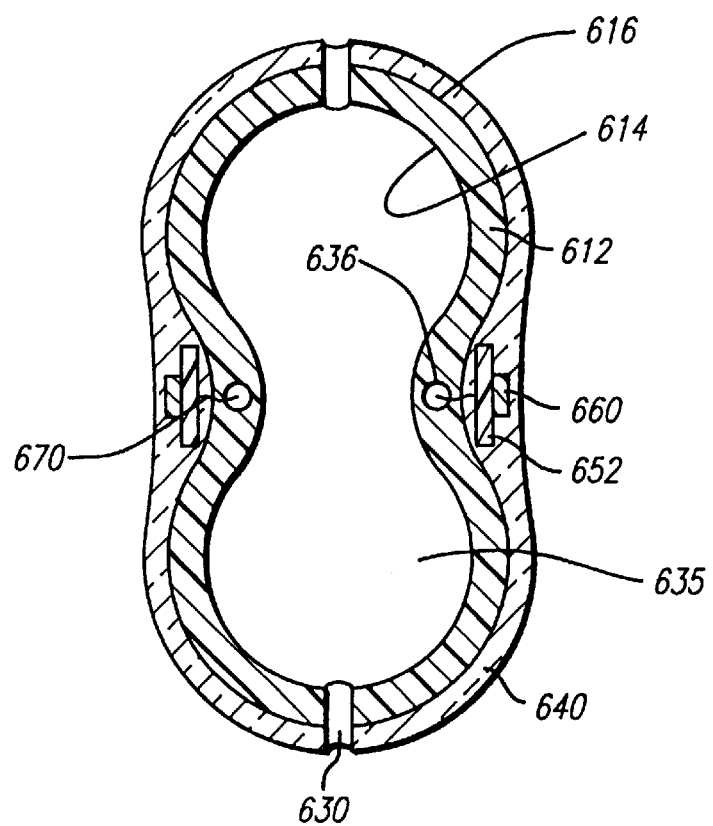
FIG. 14 is a forward view of the sixth embodiment of the catheter of the present invention.

FIGS. 13 and 14 show a sixth embodiment of the catheter of the present invention. A main housing or trocar 612 is composed of a biocompatible polymer. The main housing 612 is kidney shaped with indentations at its center. The inner edge of the main housing 612 defines a main lumen 635 for delivery of a drug or other fluid to the body or for draining fluid from a cavity with suction. The main lumen 612 includes drain apertures 630 disposed at various intervals through an upper and lower edge of the housing 612. The side indentations of the main housing 612 further include a plurality of internal lumens.

A plurality of insulated polyester strips 652 are disposed along the outer edge 616 of the main housing 612. More particularly, the strips 652 are bonded or welded to the housing along the indentations using known methods. Alternatively, the strips 652 may be embedded into the housing 612 during manufacture. A plurality of VCSELs chips 660 are surface-mounted onto each strip 652. Each strip 652 may further include a plurality of focusing lenses to focus the laser emitted by each VCSEL chip 460. The VCSELs are powered by an external power source (not shown) via a lead 670 extending from an end of each insulated strip 552. Each lead 670 exits the main housing 612 to the power source through an adjacent lumen 636. The main housing 612 is surrounded by an optically clear soft silicone sleeve 640 or a similar optically clear biocompatible polymer.

Having thus described a preferred embodiment of a laser catheter, it should be apparent to those skilled in the art that certain advantages of the within system have been achieved. It should also be appreciated that various modifications, adaptations, and alternative embodiments thereof may be made within the scope and spirit of the present invention. The invention is further defined by the following claims.

What is claimed is:

1. A catheter comprising:
   a housing having a main lumen defined within an inner edge of the housing;
   a plurality of subsidiary lumens disposed proximate the main lumen;
   an electrically insulated strip disposed longitudinally along an outer edge of the housing;
   a plurality of vertical cavity surface-emitting lasers disposed in the insulated strip;
   means for delivering power to the vertical cavity lasers;
   an inflatable balloon surrounding the insulated strip and communicating with the main lumen; and
   means for inflating the balloon coupled to the main lumen.

2. The catheter, as recited in claim 1, wherein the housing is generally cylindrical.

3. The catheter, as recited in claim 2, further comprising a plurality of extensions extending from an inner edge of the housing to the main lumen.

4. The catheter, as recited in claim 3, wherein each of the plurality of subsidiary lumens are disposed through one of the plurality of extensions.

5. The catheter, as recited in claim 4, wherein power is provided to the lasers via a lead disposed through one of the subsidiary lumens.

6. The catheter, as recited in claim 5, further comprising:
   a second insulated strip arranged longitudinally along the outer edge of the housing;
   a second plurality of vertical cavity surface-emitting lasers disposed in the second insulated strip;
   a third insulated strip arranged longitudinally along the outer edge of the housing;
   a third plurality of vertical cavity surface-emitting lasers disposed in the third insulated strip;
   a fourth insulated strip arranged longitudinally along the outer edge of the housing; and
   a fourth plurality of vertical cavity surface-emitting lasers disposed in the insulated strip.

7. The catheter, as recited in claim 1, wherein the insulated strip is formed of a polyetherimide material.

8. The catheter, as recited in claim 1, wherein the insulated strip is formed of a polyimide material.

9. A catheter comprising:

a housing having a main lumen defined within an inner edge of the housing;

a plurality of subsidiary lumens disposed through the housing;

an electrically insulated strip disposed longitudinally along an outer edge of the housing;

a plurality of vertical cavity surface-emitting lasers disposed in the insulated strip;

means for providing power to the plurality of lasers;

a flexible sleeve surrounding the insulated strip and the plurality of lasers.

10. The catheter, as recited in claim 9, wherein the housing is generally cylindrical.

11. The catheter, as recited in claim 10, wherein the insulated strip is formed of polyetherimide material.

12. The catheter, as recited in claim 10, wherein the insulated strip is formed of polyimide material.

13. The catheter, as recited in claim 10, wherein power is delivered to the lasers via a lead disposed in one of the subsidiary lumens.

14. The catheter, as recited in claim 10, further comprising:

a second insulated strip arranged longitudinally along the outer edge of the housing;

a second plurality of vertical cavity surface-emitting lasers disposed in the second insulated strip;

a third insulated strip arranged longitudinally along the outer edge of the housing;

a third plurality of vertical cavity surface-emitting lasers disposed in the third insulated strip;

a fourth insulated strip arranged longitudinally along the outer edge of the housing; and a fourth plurality of vertical cavity surface-emitting lasers disposed in the insulated strip.

15. A catheter comprising:

a main housing having a main lumen defined therethrough;

a first extended housing extending from the main housing and having a first extended lumen in communication with the main lumen;

a second extended housing extending from the main housing and having a second extended lumen in communication with the main lumen;

a first plurality of subsidiary lumens disposed through the first extended housing;

a second plurality of subsidiary lumens disposed through the second extended housing;

an electrically insulated strip disposed longitudinally along an outer edge of the first extended housing;

a first plurality of vertical cavity surface-emitting lasers disposed in the first insulated strip;

a second electrically insulated strip disposed longitudinally along an outer edge of the second extended housing;

a second plurality of vertical cavity surface-emitting lasers disposed in the second insulated strip; and means for delivering power to the vertical cavity lasers.

16. The catheter, as recited in claim 15, further comprising:

a first guidewire lumen disposed through the first extended housing;

a second guidewire lumen disposed through the second extended housing;

a first guidewire disposed in the first guidewire lumen; and a second guidewire disposed in the second guidewire lumen.

17. The catheter, as recited in claim 15, wherein power is delivered to the first plurality of lasers via a lead passing through one of the first plurality of subsidiary lumens, and wherein power is delivered to the second plurality of lasers via a second lead passing through one of the second plurality of subsidiary lumens.

18. The catheter, as recited in claim 15, further comprising:

a first optically clear tube surrounding the first extended housing; and a second optically clear tube surrounding the second extended housing.

19. A catheter comprising:

a housing having a main lumen defined within an inner edge of the housing;

a first indentation along a first side edge of the catheter;

a second indentation along a second side edge of the catheter;

an electrically insulated strip disposed longitudinally along the first indentation;

a second electrically insulated strip disposed longitudinally along the second indentation;

a first plurality of vertical cavity surface-emitting lasers disposed in the first insulated strip;

a second plurality of vertical cavity surface-emitting lasers disposed in the second insulated strip; and means for providing power to the first and second pluralities of lasers.

20. The catheter, as recited in claim 19, further comprising a plurality of draining apertures disposed along an edge of the housing.

21. The catheter, as recited in claim 20, wherein the housing is optically clear.

22. The catheter, as recited in claim 21, wherein the housing is composed of a biocompatible polymer.

* * * * *